United States Patent
Van Oorschot et al.

(10) Patent No.: US 9,704,372 B2
(45) Date of Patent: Jul. 11, 2017

(54) SLEEP POSTURE ALERTING APPARATUS AND METHOD

(71) Applicant: NIGHTBALANCE B.V., Delft (NL)

(72) Inventors: Thijs Van Oorschot, The Hague (NL); Eline Christiane Van Beest, The Hague (NL)

(73) Assignee: NIGHTBALANCE B.V., The Hauge (NL)

( * ) Notice: Subject to any disclaimer, the term of this patent is extended or adjusted under 35 U.S.C. 154(b) by 1 day.

(21) Appl. No.: 14/378,608

(22) PCT Filed: Feb. 27, 2013

(86) PCT No.: PCT/NL2013/050122
§ 371 (c)(1),
(2) Date: Aug. 13, 2014

(87) PCT Pub. No.: WO2013/129924
PCT Pub. Date: Sep. 6, 2013

(65) Prior Publication Data
US 2015/0170495 A1    Jun. 18, 2015

(30) Foreign Application Priority Data
Feb. 27, 2012    (NL) .................................. 2008359

(51) Int. Cl.
*A61B 5/11*    (2006.01)
*G08B 21/06*    (2006.01)
(Continued)

(52) U.S. Cl.
CPC ............ *G08B 21/06* (2013.01); *A61B 5/1116* (2013.01); *A61B 5/4561* (2013.01);
(Continued)

(58) Field of Classification Search
CPC .................................................... A61B 5/4806
(Continued)

(56) References Cited

U.S. PATENT DOCUMENTS

| 4,617,525 A | 10/1986 | Lloyd |
| 5,081,447 A * | 1/1992 | Echols ...................... A61F 5/56 200/DIG. 2 |

(Continued)

FOREIGN PATENT DOCUMENTS

| EP | 2263620 A1 | 12/2010 |
| JP | S5275893 A | 6/1977 |

(Continued)

OTHER PUBLICATIONS

International Search Report and Written Opinion issued Oct. 28, 2013, corresponding to International Patent Application No. PCT/NL2013/050122.
(Continued)

*Primary Examiner* — Steven Lim
*Assistant Examiner* — Benyam Haile
(74) *Attorney, Agent, or Firm* — Zareefa B. Flener; Flener IP Law

(57) ABSTRACT

A sleep posture alerting method, wherein the sleep posture of a person is detected. The person is automatically alerted by a stimulus generated by an alerting device when the sleep posture is out of a predetermined body posture range. A stimulus variation is effected by the alerting device.

19 Claims, 3 Drawing Sheets

(51) Int. Cl.
*A61F 5/56* (2006.01)
*A61B 5/00* (2006.01)
*A61M 21/00* (2006.01)
*A61B 5/01* (2006.01)

(52) U.S. Cl.
CPC .............. *A61B 5/4818* (2013.01); *A61F 5/56* (2013.01); *A61B 5/01* (2013.01); *A61B 5/4806* (2013.01); *A61B 5/4809* (2013.01); *A61B 5/4815* (2013.01); *A61B 2560/0209* (2013.01); *A61M 2021/0005* (2013.01); *A61M 2021/0022* (2013.01); *A61M 2021/0083* (2013.01)

(58) Field of Classification Search
USPC ....................................................... 340/573.7
See application file for complete search history.

(56) References Cited

U.S. PATENT DOCUMENTS

| | | | | |
|---|---|---|---|---|
| 5,477,867 | A * | 12/1995 | Balkanyi | G08B 3/10 128/848 |
| 5,555,891 | A * | 9/1996 | Eisenfeld | A61B 5/0809 600/534 |
| 2003/0199945 | A1 | 10/2003 | Ciulla | |
| 2008/0091114 | A1* | 4/2008 | Min | A61B 5/0537 600/508 |
| 2010/0100004 | A1* | 4/2010 | van Someren | A61B 5/0008 600/549 |
| 2012/0253220 | A1* | 10/2012 | Rai | A61B 5/4806 600/544 |
| 2013/0181841 | A1* | 7/2013 | Iizuka | A61B 5/4815 340/575 |
| 2014/0228905 | A1* | 8/2014 | Bolea | A61N 1/0556 607/42 |

FOREIGN PATENT DOCUMENTS

| | | |
|---|---|---|
| JP | 2008000222 A | 1/2008 |
| WO | 2010/048985 A1 | 5/2010 |
| WO | 2010141893 A2 | 12/2010 |
| WO | WO 2011139141 A1 | 11/2011 |
| WO | 2012021617 A2 | 2/2012 |

OTHER PUBLICATIONS

Search Report research of prior art completed on Oct. 18, 2012, corresponding to Dutch priority applciation NL 2008359.
Chinese Office Action dated Aug. 29, 2016 for related Chinese Application (CN201380011168.6).
Australian Patent Examination Report No. 1, for related Australian Application (AU2013226620), dated Oct. 25, 2016.

* cited by examiner

SLEEP POSTURE ALERTING APPARATUS AND METHOD

The present invention relates to a sleep posture alerting apparatus, comprising
 an electronic control unit,
 a body posture detecting sensor operatively connected to the control unit for detecting the posture of the body, and
 an alarming device operatively connected to the control unit,
wherein, the sleep posture alerting device has a normal operational mode, in which—when the posture of the body detected by the sensor exits a predefined posture range—the control unit sends an alarm signal to the alarm device, and the alarming device generates an alarm based on the signal received from the control unit, to alert said person.

Such an apparatus is disclosed in WO 2011/139141.

It is an object of the invention to provide an improved sleep posture alerting apparatus.

This object is achieved by a sleep posture apparatus of the above described type, wherein the alarming device is configured to generate different alarm stimuli, and in that the control unit is programmed to send an alarm signal to the alarming device such that a stimulus variation is effected by the alarming device.

It is noted here that the term "alerting device" in this application, and in particular in the appending claims, can mean an alerting device that can generate one type of alert stimulus (e.g. vibrotactile, tactile, electromagnetic, auditive), but can also mean an assembly of alerting devices, each of which is able to generate a certain type of alerting stimulus (e.g. vibrotactile, tactile, electromagnetic, auditive).

The present invention also relates to a sleep posture alerting method, wherein the sleep posture of a person is detected and wherein the person is automatically alerted by a stimulus generated by an alerting device when the sleep posture is out of a predetermined body posture range, wherein a stimulus variation is effected by the alerting device.

When providing the same stimulus, habituation occurs. Therefore the present invention proposes to use a stimulus variation in order to prevent this habituation effect.

The stimulus variation may comprise a variation in type of stimulus (vibrotactile, tactile, electromagnetic, auditive, (bone) conduction or a combination of stimulus types previously mentioned).

Alternatively or in addition the stimulus variation can comprise a variation in strength or amplitude of the stimulus.

Furthermore, alternatively or in addition, the stimulus variation can comprise a variation in the length of a stimulus and/or in the frequency of the stimulus.

Also, alternatively or in addition, the stimulus variation can comprise a variation in the interstimulus interval.

Moreover, it is possible to give the stimulus on different locations on the body of a patient, such that the stimulus variation can comprises a variation in the location where the stimulus is given.

The variation type as described above can be randomised. Also the type of variation within a specific form of the stimulus can be randomised.

Discontinued habituation seems to occur when a stimulation is recognised but then changes. To stimulate recognition therefore, one type of stimulus is repeated.

According to one aspect of the invention a certain alarm stimulus is repeated and then the stimulus is changed based on a certain external input variable measured by a detecting device, wherein the detecting device comprises a body posture detecting sensor combined with a timer to determine the reaction time (of body posture change) to the generated stimulus, and wherein the variable is the event of a (predetermined) time increase in reaction time compared to the previous reaction time (or an average of previous reaction times).

As such, the stimulus remains the same over a set period of time, a set number of previous stimulus rounds or types or when no (predetermined) significant changes in the subject is seen in for example their conscious or unconscious (body) response at any autonomic or non-autonomic level. So for example, the variation type as described above can remain the same based on similar responses, response times, learning effects, therapy progress, therapy results, therapy period or sleep architecture. An additional example may be to remain with the same stimulation in the event of a similar reaction time, the latter meaning that the previous reaction time (t1) is, within a certain margin, equal to the last reaction time (t2).

As long as the given stimulus remains within the margin of a 'good reaction' (t1≈t2) as described above, the device will continue to provide the preceding stimulus, not further changing any characteristics. So for example a user has a good reaction to stimulus A, then the next stimulus that is given when needed, will be the same stimulus A.

Next, to avoid the habituation, at a certain point the stimulus is (automatically) changed. This can be either after a set period of time, a set number of previous stimulus rounds or types or when a change in the subject is seen in for example their conscious or unconscious (body) response at any autonomic or non-autonomic level. So for example, the variation type as described above can be adapted to the response, response time, learning effect, therapy progress, therapy results, therapy period or sleep architecture. An additional example may be, at the moment of an increased reaction time (so the previous reaction time (t1) is shorter then the last reaction time (t2)), to change the stimulation. Then, the stimulation is changed to a different variation. This change may be, as previously described, in stimulus types, levels, frequencies, strengths, lengths, locations, amplitudes and/or interstimulus intervals. Additionally, all can vary going up or down. In doing that, habituation is discontinued and the learning effect maintained or increased.

An important aspect of the invention is that, different users show and/or experience different optimal nightly stimulus types, levels, locations, frequencies, strengths, lengths, amplitudes and/or interstimulus intervals. To accustom individual stimulus optimisation, stimulus types, levels, frequencies, strengths, lengths, locations, amplitudes and/or interstimulus intervals can be adapted towards the optimal subject reaction.

When non-optimal reaction by the subject is measured (for example, a subject does not respond to the stimulus), the stimulus (automatically) changes to a more severe or different stimulus. This ensures the effectiveness of the stimulus regardless the user. On the other hand, when optimal results are measured (for example, subject reacts very fast to the stimulus), the stimulus (automatically) stays the same, or changes to less severe stimulus. This has two main benefits; it is ensured that subjects have minimal stimulus interventions during their sleep, still evoking their reaction. And secondly, this can guide the learning process to a point where no externals stimulus is needed to avoid certain (nightly) behaviour (for example sleeping on the back).

The above processes can be endlessly repeated. The above processes can range between a lower limit and upper limit in stimulus types, levels, locations, frequencies, strengths, lengths, amplitudes and/or interstimulus intervals. The lower limit can be no stimulus at all.

The above processes can also be used to change between types of stimuli (vibrotactile, tactile, electromagnetic, auditive or a combination of stimulus types previously mentioned) to adjust the stimuli to the reaction of the user.

Another aspect is that, the whole of the sleep position trainer can be paused, to start working again after a set period of time, or based on behavioural changes of the subject, or based on whether or not a subject is already sleeping etc. This pause can be optional to be indicated or activated by the user. The pause periods may vary in time. The pause periods could also be pre set at certain moments, automatically by the device or pre-set by the user. So for example, there are always two pause moments during the night, one during the first part of sleep, one towards the end of the sleep. Or whatever a user prefers. The pause options could also increase or decrease over time, to provide a period to get used to the device, or to provide a learning effect (so if someone wants to test if they have learned not to sleep on their back they could record this during the increasing pause moments). Also this pause can be based on (behavioural) indications such as the occurrence or non-occurrence of sleep related outcomes (such as apnoeas, or snoring for example).

Sometimes users might be disturbed by the sleep position trainer during the night, which causes them to take off the device. In their sleepiness, they can forget to turn off the device. Consequence is that, in a wrong position, the device could be vibrating all night until the battery empties. Furthermore, the data representation of one's night of sleep will be distorted. An aspect of the invention is that the apparatus uses it's temperature sensor to activate the sensor only when used. Based on a temperature range at around body temperature, the sensor is active (possibly after switching the device on with the regular on/off switch). So for example at temperatures below the body temperature range the sensor is or becomes not active (e.g. when the sensor is not worn), or at temperatures above the body temperature range (e.g. when someone lays the sensor on a radiator for example). The unexpected effect of using the body temperature range to activate the device is that the device takes time to cool down when not in use (and within the housing of the device, the temperature sensor), and the other way around, it also needs time to warm up. So although the sensor may be switched on by a user, the sensor may not be at the right temperature yet to be active. This allows users to get accustomed of wearing the device and gently fall asleep before it is activated.

In general humans tend to sleep lighter towards the end of their sleep. More specifically, humans generally sleep lighter during approximately the second half of their night. Another aspect of the invention lies in that the apparatus is arranged and configured to automatically change the intensity or type of the stimulus during the second half of their night. To this end the level of the feedback to the patient (e.g. audible, tactile, vibro-tactile, movement, light, smell) is preferably decreased. It is also possible to increase the feedback, but as the patient is usually sleeping lighter during the second part of their night, a decreased level of feedback is usually sufficient to alarm the patient. This change can be set to occur after a certain period of time, or determined by the patient himself, or automatically set by changing externally measured circumstances (e.g. posture, movement, arousal, sleep, depth of sleep). This change could also occur gradually over the time of one night.

Another aspect of the invention provides for a pre-warning signal as an introduction that an alarm is upcoming. The pre-warning signal has such a level that it is only slightly noted by the patient and that it does not disturb the sleep. The pre-warning signal is not necessarily meant to evoke a reaction by the user (for example, a position change or awakening), but merely to prepare a user of the upcoming feedback, consciously or unconsciously. That way, users are less surprised when the regular alarm feedback cycle starts at a certain level of intensity. The case might be however, that a user reacts to the pre-warning. After a certain time delay, in the event that an undesired position is still detected the regular alarm feedback cycle starts. This delay time may vary over periods of the night, over periods of use (e.g. the beginning of use versus over a certain period of time of use), or they could be preset by a user. The delay time may also gradually change over any of the preceding periods. An advantage is that the pre-warning prevents that the patient is woken by the regular alarm, because the user is prepared by the pre-warning. The pre-warning could be dependent or independent of the set alarm types, levels, frequencies, strengths, lengths, locations, amplitudes and/or interstimulus intervals.

In a further aspect of the invention it is envisaged that if a patient for example has stopped sleeping with the sensor, or has not used the sensor for a certain period of time, the sleep posture alerting apparatus resets itself to another mode, such that when it is reused again it starts again with a training program. When the apparatus is reset, the selection of the mode (what program) the apparatus is reset to can be set by the user, or based on external factors. The reset can be set to occur after a certain period of time, or determined by the patient himself, or automatically set by changing externally measured circumstances (e.g. posture, movement, arousal, sleep, depth of sleep). For example in the event a certain level of usage—e.g. a lower threshold value—is reached which is monitored, the apparatus can reset itself to another mode.

Often is seen that users enjoy waking up in a relaxed way, being able to sleep in all positions. Another aspect of the invention lies in that the intensity or type of the stimulus is changed towards the end of the night or the end of the sleeping period, wherein preferably, there is an end period before waking up in which the user does not receive any feedback. According to this aspect the apparatus is arranged and configured to automatically change the intensity or type of the stimulus towards the end of the night. Preferably, there is a 'wake up period', where the user does not receive any feedback from the device. During this period the device does not actively provide alarm stimuli. This change can be set to occur after a certain period of time, or determined by the patient himself, or automatically set by changing externally measured circumstances (e.g. posture, movement, arousal, sleep, depth of sleep).

With the use of the device, users like to see their progress. Yet another aspect of the invention are diagnosis periods, in which the device is only recording and not providing feedback. These diagnosis periods could be set for a part or parts of the night, sleep, training period, or period of use. These diagnosis periods could be automatically generated, based on behaviour, moment in sleep, or they could be set by the user themselves. The diagnosis moments could also increase or decrease over time, to accustom a period of gradually learning not to sleep on the back, or to accustom a positive learning effect (so if someone wants to test if they have learned not to sleep on their back they could record this during the increasing diagnosis moments).

Further embodiments of the apparatus according to the invention are defined by dependent claims 2-21.

Further embodiments of the method according to the invention are defined by dependent claims 23-36.

The invention will be elucidated in the following description with reference to the drawings, in which.

Figure 2:
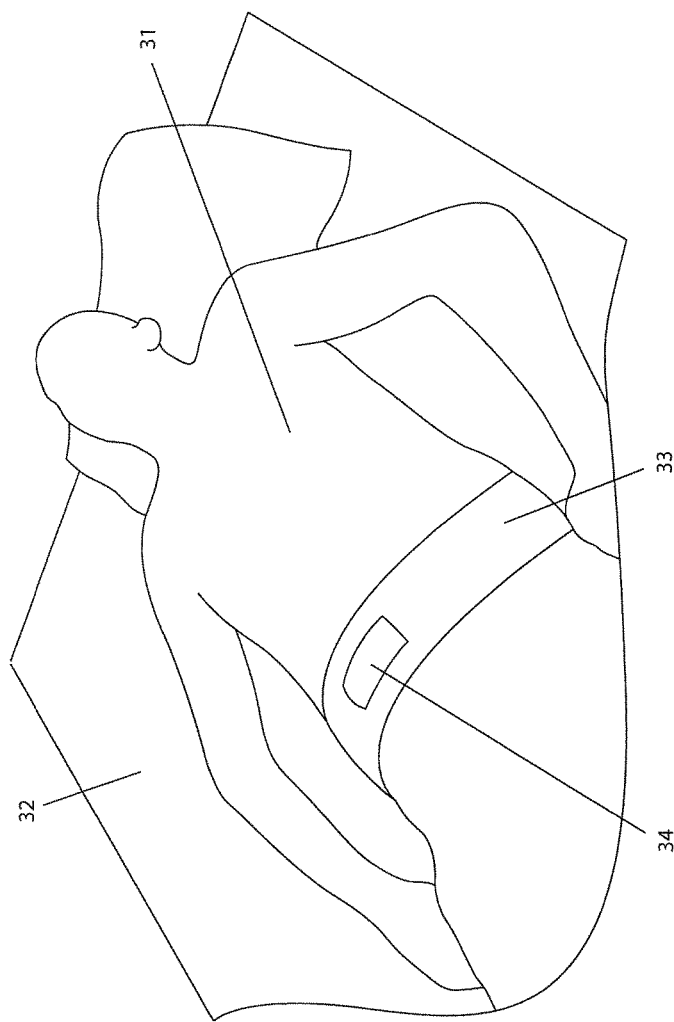
FIG. 2 shows schematically a lying person wearing an apparatus according to the invention on his body by means of a strap.
Figure 3:
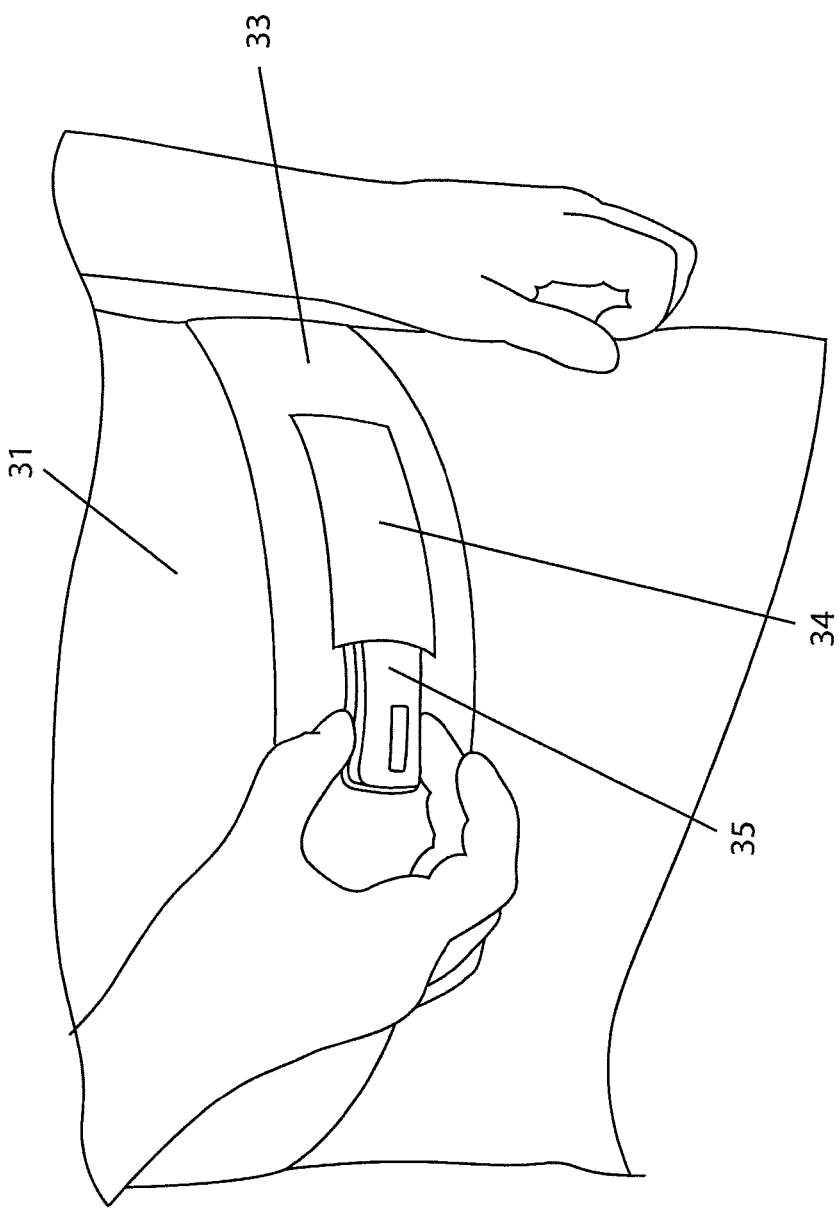
FIG. 3 illustrates how the apparatus is arranged on the strap of FIG. 2.

In FIG. 2 is shown a person 31 lying on a bed 32. The person 31 is wearing a strap 33 around his waist. The strap may also be worn around the chest or other position on the torso, around the neck or the head. In the middle of the strap 33 a pocket 34 is arranged in which a sleep posture alerting apparatus 35 is received as can be seen in FIG. 3.

Instead of a strap the apparatus 35 may also be worn in a dedicated pocket in a tight shirt. It is also possible to use a clip to attach the apparatus to one's hair, body, ear, a strap, belt or underwear, possibly underwear in which the device can be put. It is also possible to use a head cap, beanie or headband to wear or attach the apparatus to one's head. Other means like buttons, stickers, Velcro or other attaching methods could be used to place the device on nightwear, headbands, hair or directly on the skin. Also rings that use fabric (of for example a t-shirt) to hold the invention in place could be possible. Also nose plugs, earplugs or ear covers to hold the invention in place could be options. Also other means for attaching the apparatus 35 to the body are conceivable. Essential is only that the apparatus is attached to the users body, in particular to the torso and/or the neck and/or head, so that the movements and orientation of the body and/or the neck and/or the head of the user 31 are correctly related to the movements and orientation of the apparatus 35.

Figure 1:
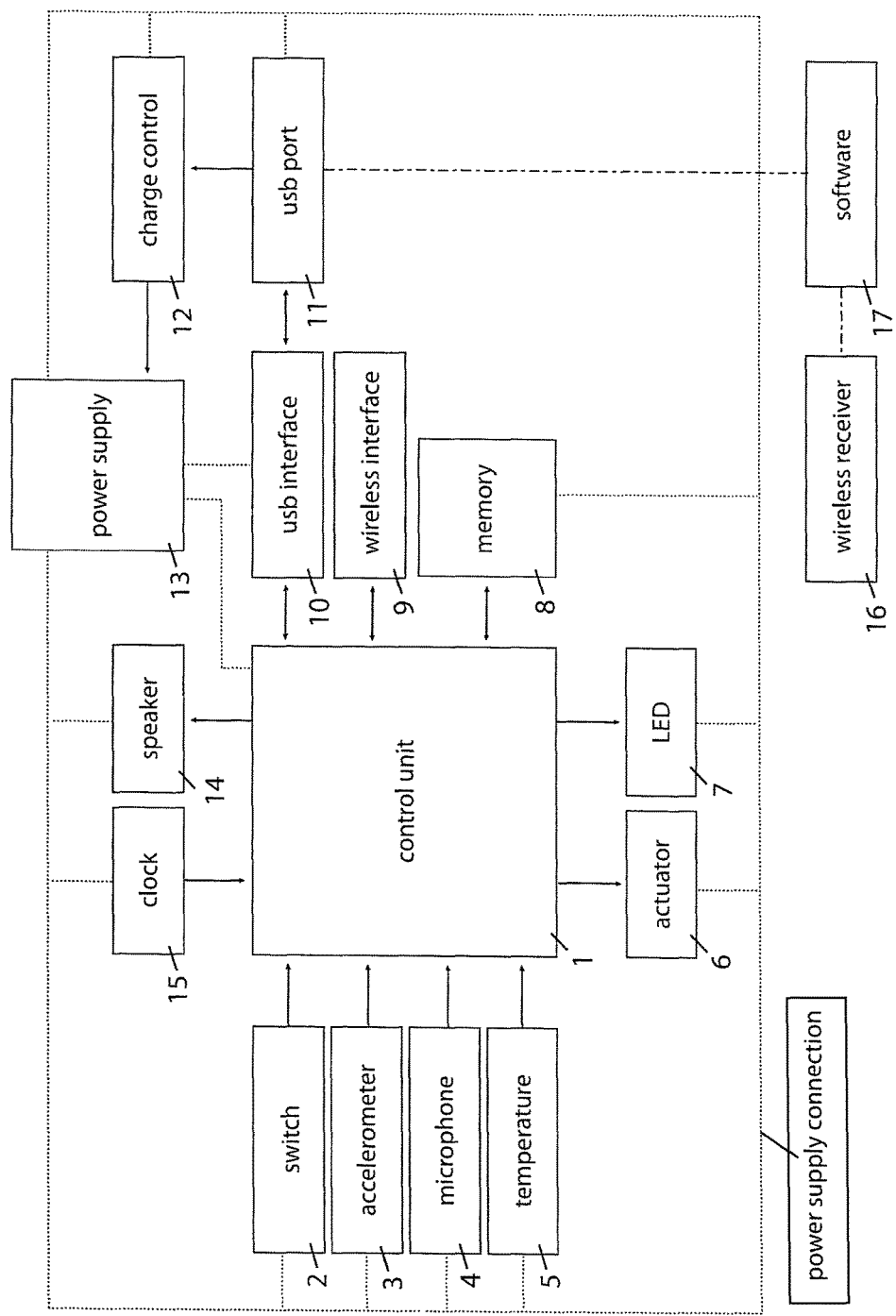
FIG. 1 shows diagrammatic representation of a preferred embodiment of the apparatus according to the invention.

FIG. 1 is an illustration of a possible component structure of the apparatus 35. The components are all directly or indirectly connected to control unit 1. The control unit 1 enables the communication between the different components and the interpretation of the signals in between the components. The communication and interpretation of the signals is defined through a method, or so-called algorithm, of the control unit 1.

The control unit is in particular a programmable microcontroller which enables the communication between and the control of the hardware components. The control unit makes it possible to transfer all the signals between the different hardware components and external applications/products connected to the device. Furthermore it enables the programming of the behaviour of the apparatus and so to tell it how to respond to situations (e.g. accelerometer values, feedback, snoring sound, upright posture, and more).

The apparatus 35 furthermore includes a gravity-actuated sensor 3 (cf. FIG. 1). Preferably the gravity actuated sensor is an electronic three-axes accelerometer/3-axes MEMS accelerometer to define the posture of the apparatus in three dimensions which is directly related to the posture of the body of the user 31. The introduction of a MEMS accelerometer is preferred because of the high frequency of measurements and fast response time to small changes in acceleration.

The apparatus also includes an alert device. In principle any type of alert that is noticed by the user in the specific circumstance, e.g. smell, sound, sight, taste and tactile electronic stimulation, vibrotactile, (bone) conduction or any other may be applied. The alert device may for example be adapted for vibrotactile stimulation of the person 31, preferably by a vibration motor 6. The use of vibrotactile feedback may be preferable because it is comfortable in that it does not hurt or injure the user 31 (like with electronics shocks) and does not disturb the sleep rhythm of the user 31 or partner of the user 31, like e.g. with sound.

Additionally the alert device may include a speaker 14 for audible feedback to the user 31. Also the alert devices may include other type of alert sub-devices (generating e.g. smell, sight, taste and tactile-electronic stimulation, (bone) conduction or any other) such that a variation of alert types can be given to the user. When providing the same stimulus, habituation occurs. Therefore the present invention proposes to use a stimulus variation in order to prevent this habituation effect. The stimulus variation may comprise a variation in type of stimulus, e.g. vibrotactile, tactile, electromagnetic, auditive or a combination of stimulus types previously mentioned.

Alternatively or in addition the stimulus variation can comprise a variation in strength or amplitude of the stimulus. Furthermore, alternatively or in addition, the stimulus variation can comprise a variation in the length of a stimulus and/or in the frequency of the stimulus. Also, alternatively or in addition, the stimulus variation can comprise a variation in the interstimulus interval. Moreover, it is possible to give the stimulus on different locations on the body of a patient, such that the stimulus variation can comprises a variation in the location where the stimulus is given The variation type as described above can be randomised. Also the type of variation within a specific form of the stimulus can be randomised.

The alert device may additionally be provided with a connection to other devices to enable remote monitoring by another individual, for example caretakers, nurses, parents or other family members.

The apparatus 35 may include a display, preferably a LED display 7 to give visual feedback to the user. The introduction of a LED will enable the apparatus 35 to transfer information using visual feedback to the user 31 to indicate e.g. battery status, stored events, operation mode, progress, occupation, and more.

The apparatus 35 may have a sound sensor, preferably a microphone 4 to detect noise or sound level from the environment, possibly to detect snoring, possibly to register disturbances. The introduction of a sound sensor enables the detection of snoring sounds so that even if the user is snoring in the desired position a type of feedback is activated to change position or posture (e.g. so that the partner does not have to do so) and therefore the device is optimised to prevent snoring.

The apparatus may be provided with a data storage device, preferably a memory 8 to store detected and measured events. Registering events makes it possible to gather information about what is going on at a certain moment during the sleep. This can be used at another moment in time to determine, inform, diagnose, help and/or advise users or others of various elements. This may be feedback to the user, information about sleeping/sleep monitoring, combine the storage of events with a certain action to indicate something to the user, make calculations, averages, figures, etcetera.

The apparatus may be provided with a feature to transfer stored data, preferably a USB interface 10 to enable connecting the apparatus 35 to a personal computer. The ability to transfer stored data enables a lot of options to combine the apparatus 35 with other appliances/software/products to enhance the capabilities of the stored events. This way information can be transferred or exchanged between appliances/products/software to offer new features to the user or give them more insight in the information stored in the apparatus 35.

The apparatus 35 may have external communication through a USB interface 10, but alternatively or additionally through a wireless interface 9 for communication with a computer or other devices. The communication with external devices, e.g. a personal computer, baby phone, or other, enables the exchange of information between those devices and enables options for information feedback, remote monitoring, remote data uploads or remote control.

The apparatus 35 has a power supply 13, preferably an integrated battery to enable wireless use of the apparatus 35. The integration of the battery makes it possible to use the apparatus 35 wherever wanted without the need of a wall plug. Furthermore it makes the apparatus 35 wireless, which improves the comfort for the user 31 and the freedom to move in/around/away from the bed or sleeping area.

The apparatus may have a charging system 11, 12, preferably including a USB port 11 which enables charging the battery of the apparatus 35 through an adapter or a personal computer. Charging the battery with a charging system 11, 12 means the user does not have to open up the apparatus 35 and/or to change the batteries to keep using the product. This minimises the occurrence of problems to the apparatus 35 and makes it easier to supply it with required power. Preferably a charging system based on induction or exchange of movement to enable the charging of the battery without the need for an opening in the housing, such that the apparatus can be made moisture/waterproof.

The apparatus 35 may include a temperature switch, preferably an integrated circuit temperature switch to define overheating of electronic components to disconnect power supply if temperature exceeds a certain threshold value. Thus, to prevent overheating of the device and minimise the risk.

The apparatus may include a temperature detection means, preferably an integrated temperature sensor 5, additionally an external temperature sensor connected to the device to detect for example body temperature to define sleep comfort, which may be especially important for monitoring babies. The introduction of an integrated temperature sensor 5 enables measurement of the temperature of the body to enable more options of feedback and sleep information. First of all the user can be indicated of a high temperature during sleep to improve the quality and comfort of the sleep. Also it is possible to alarm in certain situations and information can be given to the user about the body temperature during sleep; especially with babies or children. For babies, correct temperature of the body during sleep is very important.

Furthermore the apparatus 35 may be provided with additional integrated detection means (not shown), like e.g. a sound sensor, shock sensor, humidity sensor and more for additional functions like detection of respiration, snoring sound, environmental influence factors and more. Moreover the apparatus 35 may have connectors (not shown) for external sensors; e.g. position sensors, shock sensors, respiration sensors and more for additional functions like detection of blood saturation, brain activity, airflow, respiration, breathing pattern, heart rate, muscle movement, snoring, apnoea and more.

The apparatus 35 includes an internal clock 15, preferably crystal oscillator to provide the time and data to the control unit. The internal clock 15 enables the registration of events in relation with time to create a timestamp for the event. In this way the time the event took place can be defined more precise for storage into the memory 8 and/or feedback (alert) through information given to the user 31.

The apparatus may be supplied with software which can be loaded on a computer. The software program may be used to download, store, analyse, display, visualise and/or transfer data from the apparatus to the computer 35. The software program enables the interpretation, visualisation and comparison of the events and data stored by the apparatus to enable feedback of events. This way events registered at a certain moment can be communicated at another moment in time through which the user 31 can be informed about their behaviour. The most beneficial result of this is that it is possible to guide and train the user 31 into sleeping with an improved sleeping posture by giving more insight and to stimulate the use of the apparatus 35. This can also be used for guidance, monitoring or control by externals like for example a parent, doctor or nurse. Preferably the software can be used to combine parameters, values, functions, and more between the proposed invention and external products or appliances that can be connected to the personal computer or through the world wide web.

The apparatus 35 has a switch 2 which is connected to the control unit 1 to activate it. Whenever the apparatus 35 is activated, the accelerometer 3, microphone 4 and temperature sensory means 5 execute measurements to be transferred to the control unit 1 for interpretation.

The accelerometer 3 returns values for the accelerations measured in all three dimensions x, y and z. From these values the activity, movement and or position can be derived. The microphone 4 returns values for the frequency and amplitude of the measured sound. The temperature sensory means 5 returns values for the temperature measured in its environment (e.g. body temperature, device temperature and more).

Whenever the signals from the accelerometer 3, microphone 4 or temperature sensory means 5 exceed a predefined threshold, e.g. undesired body posture, occurring apnoeas or snoring, when interpreted by the control unit 1 the actuator 6 (e.g. a vibration motor) is activated to indicate the user 31 that the body position needs to be changed.

Whenever visual feedback to the user is needed the control unit 1 activates the LED display 7 to switch on the light of the LED display 7 in a predefined sequence.

Whenever an event takes place within the control unit 1 which is predefined to be stored it is done so by sending a signal from the control unit 1 to the internal memory 8. The control unit 1 can also retrieve information stored into the memory 8 whenever necessary.

Whenever a wireless interface 9 is connected to the control unit 1 the apparatus 35 is able to communicate through the wireless interface 9 with a wireless receiver 16 of an external device.

Whenever an external device is connected to the device through the USB port 11 signals are exchanged between the USB port 11 and the control unit 1 through the USB interface 10. The USB interface 10 translates the signals from the USB port 11 into signals to the control unit 1 and vice versa.

Whenever an external device is connected to the device through the USB port 11 power can be transferred to the power supply 13 with the use of a charge control 12. The charge control 12 enables the transfer of electronic power from the USB port 11 to the power supply 13.

The power supply 13 is connected to all components within the device which have to be supplied with electronic power. The electronic power transferred from the power supply 13 to the control unit 1 is measured by the control unit 1 to define the status of the power supply 13.

Whenever a speaker 14 is connected to the control unit 1 it is possible to sound an alarm or produce sound through the speaker 14.

The clock 15 is directly connected to the control unit 1 to provide the control unit 1 with the values to define the date and the time. This information from the clock 15 is used to store the date and time for events stored from the control unit 1 into the memory 8.

Whenever communication through the USB port 11 or wireless interface 9 is possible with software from an external device 17 the control unit 1 can exchange information or programs with the software 17.

The invention claimed is:

1. A sleep posture alerting apparatus for a person, comprising
    an electronic control unit;
    a body posture detecting sensor operatively connected to the electronic control unit and configured to detect a posture of a body of the person and generate a plurality of posture signals based on the posture;
    a memory operatively connected to the electronic control unit;
    a timer operatively connected to the electronic control unit; and
    an alarming device operatively connected to the electronic control unit and configured to generate a plurality of alarm stimuli;
    wherein the electronic control unit is configured to
        receive a first posture signal from the body posture detecting sensor,
        determine whether the body exited a predefined posture range based on the first posture signal,
        generate an alarm signal if the body exited the predefined posture range,
        send the alarm signal to the alarming device causing the alarming device to generate a first alarm stimulus to alert the person,
        start the timer based on the alarm signal,
        receive a second posture signal from the body posture detecting sensor based on a change of the posture of the body of the person,
        determine a current reaction time between the start of the timer and receiving the second posture signal,
        store the current reaction time in the memory,
        determine an average reaction time based on at least one previously determined and stored reaction time,
        determine whether the difference between the current reaction time and the average reaction time is outside a predefined margin,
        generate a change signal if the difference between current reaction time and the average reaction time is outside the predefined margin, and
        send a change signal to the alarming device causing the alarming device to generate a second alarm stimulus to alert the person, wherein the second alarm stimulus is different than the first alarm stimulus.

2. The sleep posture alerting apparatus according to claim 1, wherein a type of the first alarm stimulus and the second alarm stimulus comprise at least two of the following: vibrotactile, tactile, electromagnetic, auditive, bone conduction, or a combination thereof.

3. The sleep posture alerting apparatus according to claim 1, wherein each of the plurality of alarm stimuli has a characteristic comprising at least one selected from the group consisting of an amplitude, a strength, a length, a frequency, an interstimulus interval, a melody, a message, and a location.

4. The sleep posture alerting apparatus according to claim 3, wherein at least one of the amplitude and the strength of the second alarm stimulus is different from at least one of the amplitude and the strength of first alarm stimulus.

5. The sleep posture alerting apparatus according to claim 3, wherein the length of the second alarm stimulus is different from the length of the first alarm stimulus.

6. The sleep posture alerting apparatus according to claim 3, wherein the frequency of the second alarm stimulus is different from the frequency of the first alarm stimulus.

7. The sleep posture alerting apparatus according to claim 3, wherein the interstimulus interval of the second alarm stimulus is different from the interstimulus interval of the first alarm stimulus.

8. The sleep posture alerting apparatus according to claim 3, wherein at least one of the melody and the message of the second alarm stimulus is different from at least one of the melody and the message of the first alarm stimulus.

9. The sleep posture alerting apparatus according to claim 3, wherein the location of the second alarm stimulus on the body is different from the location of the first alarm stimulus on the body.

10. The sleep posture alerting apparatus according to claim 1, wherein the control unit is further configured to send a pre-warning signal to the alarming device causing the alarming device to generate a pre-warning alarm stimulus as an introduction for the person that the plurality of alarm stimuli is upcoming, wherein the pre-warning signal has not the intention to evoke an active reaction of the user.

11. The sleep posture alerting apparatus according to claim 10, wherein at least one selected from the group consisting of a strength, a type, and a location of the pre-warning stimulus is dependent on the at least one selected from the group consisting of a strength, a type, and a location of the plurality of alarm stimuli.

12. The sleep posture alerting apparatus according to claim 1, wherein the alarming device is configured to automatically change a characteristic of the plurality of alarm stimuli during an end of a night.

13. The sleep posture alerting apparatus according to claim 12, wherein the alarming device is configured not to generate the plurality of alarm stimuli during the end of a night.

14. The sleep posture alerting apparatus according to claim 1, wherein the electronic control unit is further configured to receive a pause signal and pause operation of the apparatus based on the pause signal.

15. The sleep posture alerting apparatus according to claim 1, wherein the electronic control unit is further configured to receive a reset signal and reset at least one of the alarm signal, the change signal, the predefined posture range and the predefined margin.

16. The sleep posture alerting apparatus according to claim 1, wherein the body posture detecting sensor is a three-axes micro-electro mechanical system-based accelerometer.

17. The sleep posture alerting apparatus according to claim 1, wherein the alarming device is at least one selected from the group consisting of a vibration motor, an LED display, and a speaker.

18. A sleep posture alerting apparatus for a person, comprising
an electronic control unit;
a body posture detecting sensor operatively connected to the electronic control unit and configured to detect a posture of a body of the person and generate a plurality of posture signals based on the posture;
a memory operatively connected to the electronic control unit;
a timer operatively connected to the electronic control unit; and
an alarming device operatively connected to the electronic control unit and configured to generate a plurality of alarm stimuli;
wherein the electronic control unit is configured to
receive a first posture signal from the body posture detecting sensor,
determine whether the body exited a predefined posture range based on the first posture signal,
generate an alarm signal if the body exited the predefined posture range,
send the alarm signal to the alarming device causing the alarming device to generate a first alarm stimulus to alert the person,
start the timer based on the alarm signal,
receive a second posture signal from the body posture detecting sensor based on a change of the posture of the body of the person,
determine a current reaction time between the start of the timer and receiving the second posture signal,
store the current reaction time in the memory,
determine an average reaction time based on at least one previously determined and stored reaction time,
determine whether the difference between the current reaction time and the average reaction time is outside a predefined margin,
generate a change signal if the difference between current reaction time and the average reaction time is outside the predefined margin,
send a change signal to the alarming device causing the alarming device to generate a second alarm stimulus to alert the person, wherein the second alarm stimulus is different than the first alarm stimulus, and
send a pre-warning signal to the alarming device causing the alarming device to generate a pre-warning alarm stimulus as an introduction for the person that the plurality of alarm stimuli is upcoming, wherein the pre-warning signal has not the intention to evoke an active reaction of the user.

19. The sleep posture alerting apparatus according to claim 18, wherein at least one selected from the group consisting of a strength, a type, and a location of the pre-warning stimulus is dependent on the at least one selected from the group consisting of a strength, a type, and a location of the plurality of alarm stimuli.

* * * * *